(12) United States Patent
Herring

(10) Patent No.: US 10,902,238 B2
(45) Date of Patent: Jan. 26, 2021

(54) SYSTEMS AND METHODS FOR PREDICTING SEMANTICS OF A PARTICLE USING SEMANTIC SEGMENTATION

(71) Applicant: Toyota Research Institute, Inc., Los Altos, CA (US)

(72) Inventor: Patrick K. Herring, Mountain View, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 244 days.

(21) Appl. No.: 16/202,707

(22) Filed: Nov. 28, 2018

(65) Prior Publication Data

US 2020/0167546 A1    May 28, 2020

(51) Int. Cl.
| | |
|---|---|
| *G06K 9/00* | (2006.01) |
| *G06N 3/08* | (2006.01) |
| *G06K 9/62* | (2006.01) |
| *G06K 9/34* | (2006.01) |
| *G06K 9/72* | (2006.01) |
| *G16H 30/20* | (2018.01) |

(52) U.S. Cl.
CPC ........... *G06K 9/00147* (2013.01); *G06K 9/34* (2013.01); *G06K 9/6262* (2013.01); *G06K 9/726* (2013.01); *G06N 3/08* (2013.01); *G16H 30/20* (2018.01)

(58) Field of Classification Search
CPC .... G06K 9/00147; G06K 9/6262; G06K 9/34; G06K 9/726; G06N 3/08; G16H 30/20
See application file for complete search history.

(56) References Cited

U.S. PATENT DOCUMENTS

| | | | | |
|---|---|---|---|---|
| 10,650,315 B2* | 5/2020 | Mudie | .................. | G06N 3/0454 |
| 2002/0057850 A1* | 5/2002 | Sirohey | ................ | H04N 19/136 |
| | | | | 382/299 |
| 2007/0240242 A1 | 10/2007 | Modiano et al. | | |
| 2015/0302166 A1* | 10/2015 | Thomson | ................ | G16H 20/40 |
| | | | | 703/2 |
| 2017/0235852 A1 | 8/2017 | Joshi et al. | | |
| 2017/0241891 A1 | 8/2017 | Grier et al. | | |
| 2018/0322634 A1* | 11/2018 | Zimmerman | ........ | G06K 9/6267 |

(Continued)

OTHER PUBLICATIONS

Fernandes et al., "Segmentation of TEM Images Using Oscillatory Neural Networks," Proceedings XIV Brazilian Symposium on Computer Graphics and Image Processing (Oct. 2001).

(Continued)

*Primary Examiner* — Lewis G West
(74) *Attorney, Agent, or Firm* — Christopher G. Darrow; Darrow Mustafa PC

(57) ABSTRACT

System, methods, and other embodiments described herein relate to classifying semantics of a particle or other material component. In one embodiment, a method includes, in response to receiving a particle image, analyzing the particle image to identify characteristics of the particle represented in respective pixels of the particle image to produce a segmented image that groups the pixels into subregions. The method includes identifying semantics of the particle according to at least boundaries between the subregions. The semantics define expected behaviors of the particle in relation to material physics. The method includes providing the segmented image including the semantics as an electronic output.

20 Claims, 6 Drawing Sheets

(56) References Cited

U.S. PATENT DOCUMENTS

| | | | | |
|---|---|---|---|---|
| 2018/0330615 A1* | 11/2018 | Yamanaka | ............ | G06K 9/3241 |
| 2019/0043269 A1* | 2/2019 | Lin | .......................... | G06T 17/00 |
| 2019/0155973 A1* | 5/2019 | Morczinek | ........... | G06K 9/0063 |
| 2019/0252073 A1* | 8/2019 | Hsu | .......................... | G06N 3/08 |
| 2019/0278880 A1* | 9/2019 | Ma | .......................... | G06N 3/084 |
| 2019/0370955 A1* | 12/2019 | Zhang | .................. | G06T 7/0004 |
| 2020/0160094 A1* | 5/2020 | Fujimoto | ............... | G06K 9/628 |
| 2020/0167438 A1* | 5/2020 | Herring | ................... | G06K 9/00 |
| 2020/0167913 A1* | 5/2020 | Singer | ....................... | G06T 7/11 |

OTHER PUBLICATIONS

Wang, "Effects of External Stimuli on Microstructure-Property Relationship at The Nanonscale," The Pennsylvania State University, ProQuest Dissertations Publishing (Aug. 2017).

Dahmen, et al., "Feature Adaptive Sampling for Scanning Electron Microscopy", Scientific Reports vol. 6, Article No. 25350 (May 2016).

Chen et al., "Semantic Image Segmentation with DeepLab in TensorFlow," Google AI blog (Mar. 12, 2018).

\* cited by examiner

SYSTEMS AND METHODS FOR PREDICTING SEMANTICS OF A PARTICLE USING SEMANTIC SEGMENTATION

TECHNICAL FIELD

The subject matter described herein relates, in general, to systems and methods for identifying aspects of a particle, and, in particular, to using semantic segmentation to distinguish between subregions of the particle having different characteristics such that the identified subregions further inform classification of semantics of the particle.

BACKGROUND

Developing new materials and further understanding existing materials for improving batteries, and other products can be expensive and time consuming. This is especially true in relation to products that include complex materials. In general, to improve upon existing materials, developers employ a variety of metrology and simulation techniques to predict how a material will behave under different conditions and how the material may be modified to improve performance. However, present approaches to studying and understanding materials with respect to microscale characteristics (e.g., molecule level responses to stresses, etc.) are inadequate. For example, finite element analysis (FEA) is a numerical method often used in combination with complex mathematical modeling to analyze structures and compositions of materials (i.e., particles/molecules). This approach provides inferences about properties of the material and other characteristics but is generally slow and computationally intensive leading to prolonged periods of research/analysis to resolve information about a single material under a single circumstance (e.g., particular stress). These difficulties can be especially pronounced when considering the need to analyze many different compounds under different stimuli in order to identify desirable research and development directions.

SUMMARY

In one embodiment, example systems and methods relate to a manner of analyzing a particle through the use of semantic segmentation to identify characteristics of the particle embodied within an image. As mentioned previously, finite element analysis (FEA) and associated mathematical modeling techniques represent significant difficulties with respect to complexity and computational time especially when analyzing many different particles. The disclosed approach improves over prior difficulties by leveraging machine learning algorithms to automate the process of understanding the complexities of the particle and provides identification and prediction of material properties resulting in development of large scale data sets that were not previously available.

For example, in one embodiment, a disclosed system analyzes particles using microscopy images (e.g., transmission electron microscopy (TEM)). In one aspect, the microscopy images provide details of the structure and characteristics of the particle at, for example, a nanoscale i.e., particle-level. Thus, the images include fine details of the structure and are generally comprised of separate pixels that can each include a diffraction pattern from scattered electrons of a corresponding location on the particle. While the image includes a dense representation of the particle, the representation in the image, and, in particular, the diffraction patterns function to encode the noted information in such a way that the information is not explicitly evident especially to a manual review of the image.

As such, the disclosed system leverages the machine learning algorithm to analyze the image. The machine learning algorithm, in one approach, analyzes each pixel to produce a segmented image therefrom identifying subregions in the image associated with locations on the particle having similar characteristics. In analyzing the particle image, the system may leverage the machine learning algorithm to analyze multiple modalities (e.g., color, depth, diffraction patterns). In providing the segmented image, the system identifies boundaries between the areas having different characteristics as, for example, a property of labeling the separate pixels. The boundaries generally correspond with different properties of the particle in relation to, for example, how the particle may respond to different stimuli. Accordingly, the disclosed system can classify the properties or semantics of the particle at the boundaries using the noted machine learning algorithm. That is, the disclosed system classifies interfaces/boundaries between the separate segments according to the semantics of the particle.

The semantics are physical traits, otherwise referred to as physics of the particle, such as characteristics of interfaces between different regions of the particle and that are defined according to properties/types of the abutting subregions. The various types of abutting subregions influence how the particle responds to various stimuli (i.e., stresses) along the boundary. In this way, the disclosed system provides a mechanism for determining properties of particles in order to further understandings of how the particles may behave and thus provide guidance for improving the engineering of materials that comprise the particles. Moreover, the system achieves the noted results through simple computational analysis of images of the particles without the need to undertake complex research and testing on each separate particle or manually develop models.

In one embodiment, a semantics system for classifying semantics of a particle is disclosed. The semantics system includes one or more processors and a memory communicably coupled to the one or more processors. The memory stores a segmentation module including instructions that when executed by the one or more processors cause the one or more processors to analyze a particle image to identify characteristics of the particle represented in respective pixels of the particle image and to produce a segmented image that groups the pixels into subregions. The memory stores a prediction module including instructions that when executed by the one or more processors cause the one or more processors to identify semantics of the particle according to at least boundaries between the subregions. The semantics define expected behaviors of the particle in relation to material physics. The prediction module includes instructions to provide the segmented image including the semantics as an electronic output.

In one embodiment, a non-transitory computer-readable medium for classifying semantics of a particle and including instructions that when executed by one or more processors cause the one or more processors to perform one or more functions. The instructions include instructions to analyze a particle image to identify characteristics of the particle represented in respective pixels of the particle image and to produce a segmented image that groups the pixels into subregions. The instructions include instructions to identify semantics of the particle according to at least boundaries between the subregions. The semantics define expected behaviors of the particle in relation to material physics. The instructions include instructions to provide the segmented image including the semantics as an electronic output.

In one embodiment, a method for classifying semantics of a particle is disclosed. The method includes, in response to receiving a particle image, analyzing the particle image to identify characteristics of the particle represented in respective pixels of the particle image to produce a segmented image that groups the pixels into subregions. The method includes identifying semantics of the particle according to at least boundaries between the subregions. The semantics define expected behaviors of the particle in relation to material physics. The method includes providing the segmented image including the semantics as an electronic output.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Figure 1:
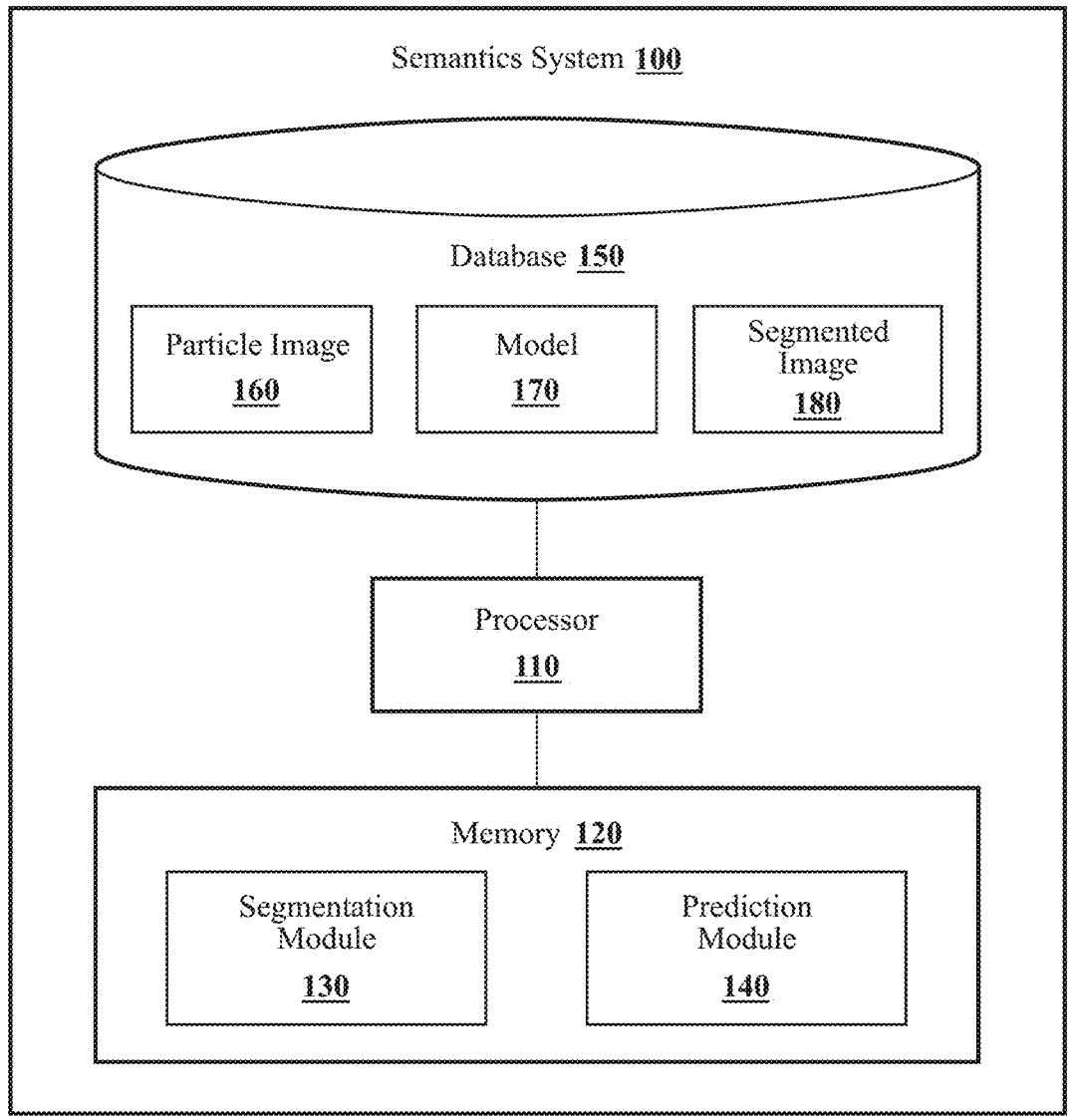
FIG. 1 illustrates one embodiment of a semantics system that is associated with identifying semantics of a particle by analyzing associated images.

Systems, methods, and other embodiments associated with inferring semantics of a particle using semantic segmentation are disclosed. As mentioned previously, difficulties with respect to complexity and excessive computational time complicate robust analysis (e.g., analysis and simulation) of many different materials and particles preventing determination of particle-level (i.e., mesoscale) behaviors/characteristics under various conditions. For example, when engineering a new material for a battery, it may be useful to analyze a wide array of materials and determine the properties of the materials under a variety of conditions, such as exposure to various chemical environments, responses to electrical current, mechanical properties, and so on. Thus, if a given analysis is to include one hundred different particles and observations of the particles under ten different conditions, then the analysis would potentially be carried out over one thousand times. When using an approach such as FEA, analyzing one thousand different tests of particles represents an excessive effort, which may be unsuitable for purposes of developing a new material. Accordingly, using FEA and mathematical modeling may cause analysis to be constrained within a smaller sample set, leading to a less robust development process. Additionally, FEA and other a-priori modeling techniques usually require a large amount of validation based on experimentally derived results, which significantly increases the amount of time and effort involved.

However, the disclosed approach improves analysis of the particles by providing an efficient mechanism to characterize the particles and generate inferences therefrom about various physical traits (i.e., semantics) of the particles thereby resolving the difficulties encountered in previous approaches. More particularly, the disclosed approach improves over prior approaches by leveraging machine learning algorithms to develop understandings of the complexities and automate identification through the use of the understandings. For example, since the physics of the material are not explicitly programmed, but rather the machine learning algorithm infers the physics from the experimentally derived data, the disclosed system improves (e.g., drastically reduces) the amount of time and effort involved in analyzing the material.

In one embodiment, a disclosed system uses microscopy images (e.g., transmission electron microscopy (TEM)) to analyze particles depicted therein. In one aspect, the microscopy images provide details of the structure and characteristics of the particle at, for example, a nanoscale i.e., particle-level. Thus, the images include fine details of the structure including high-order features and are generally comprised of separate pixels that each include, for example, a diffraction pattern from scattered electrons of a corresponding location on the particle. The diffraction patterns function to encode the information about the particle in a dense representation (i.e., fine detail about each corresponding location on the particle) in such a way that the information is not explicitly evident especially to a manual review of the image.

As such, the disclosed system leverages one or more machine learning algorithm(s) to analyze the image. The machine learning algorithm, in one approach, analyzes the diffraction pattern of each pixel to produce a segmented image identifying subregions in the image associated with locations on the particle having similar characteristics. In providing the segmented image, the disclosed system further identifies spatial relationships between pixels of various characteristics, and, in particular, identifies boundaries between the subregions having different characteristics. The boundaries generally correspond with different properties of the particle in relation to, for example, how the particle may respond to different stimuli. Accordingly, the disclosed system can classify the properties or semantics of the particle at the boundaries using the noted machine learning algorithm. That is, the disclosed system classifies interfaces/boundaries between the separate segments according to corresponding semantics that correlate with types of subregions interfacing at the boundary.

The semantics are physical traits such as attributes of interfaces between different regions of the particle that respond differently according to different characteristics of the abutting subregions. The various types of abutting subregions can cause different responses in the particle according to different stresses. Thus, the disclosed system identifies the semantics of the particle in order to provide awareness about how the particle may behave under different conditions (e.g., operating conditions of a device). In this way, the disclosed system provides a mechanism for determining properties of particles in order to further understand overall characteristics and how the particles may behave and thus improve the engineering of materials in which the particles may be included.

Referring to FIG. 1, one embodiment of a semantics system 100 that is implemented to perform methods and other functions as disclosed herein relating to analyzing images of particles is illustrated. As an initial matter, it should be appreciated, that while the semantics system 100 is illustrated as being a single contained system, in various embodiments, the semantics system 100 is a distributed system that is comprised of components that can be distributed across multiple servers, provided by a cloud-based service, and so on.

With further reference to FIG. 1, the semantics system 100 is shown as including a processor 110. Accordingly, the processor 110 may represent a distributed processing resource, an individual local processor (e.g., a CPU, GPU, or application specific processor), or the semantics system 100 may access the processor 110 through a data bus or another communication path. In one embodiment, the semantics system 100 includes a memory 120 that stores a segmentation module 130 and a prediction module 140. The memory 120 is a random-access memory (RAM), read-only memory (ROM), a hard-disk drive, a flash memory, a processor cache, or other suitable memory for storing the modules 130 and 140. The modules 130 and 140 are, for example, computer-readable instructions that when executed by the processor 110 cause the processor 110 to perform the various functions disclosed herein. Thus, as may be appreciated, in various implementations, the module 130 and 140 as envisioned herein may be integrated as a component of the processor 110, stored in an associated/accessible memory to the processor 110, implemented as a standalone electronic functional unit, and so on.

Moreover, as previously noted, in various embodiments, one or more aspects of the semantics system 100 are implemented as cloud-based services, and so on. Thus, one or more components of the semantics system 100 may be located remotely from other components and may be implemented in a distributed manner. As an additional matter, the semantics system 100 includes the database 150 as a means of storing various data elements. The database 150 is, in one embodiment, an electronic data structure stored in the memory 120 or a separate electronic data store and that is configured with, for example, routines that can be executed by the processor 110 for analyzing stored data, providing stored data, organizing stored data, and so on. Thus, in one embodiment, the database 150 stores data used by the modules 130 and 140 in executing various functions. In the embodiment, as depicted in FIG. 1, the database 150 includes a particle image 160, a model 170, and/or other information such as a segmented image 180 as may be used by the modules 130 and/or 140.

As additional explanation of the noted images prior to discussing the functionality of the semantics system 100, consider that the particle image 160 is, in one embodiment, a transmission electron microscopy (TEM) image of a particle. That is, a TEM microscope produces the particle image 160 from a sample of a particular material (e.g., lithium-based material). It should be appreciated that while a TEM microscope is discussed herein, in further approaches, the particular type of TEM microscope (e.g., conventional, scanning, etc.) may vary or other types of microscopes (e.g., x-ray) that produce similar diffraction patterns may be substituted.

In either case, continuing with the process of generating the particle image 160, the sample is, in one embodiment, a homogenous sampling of a material that includes a plurality of occurrences of the particle. Thus, the particle image 160 generally represents a focused view of the sample that embodies the single particle. Moreover, as used herein, the particle is, for example, a basic unit (i.e., molecule) of the associated material and, thus, is representative of the material overall.

In one approach, the semantics system 100 controls the TEM microscope to scan the sample using a beam of electrons. Thus, the semantics system 100 can be integrated with the TEM microscope as a single electronic system or communicate with the TEM microscope over a direct link or network connection. In either case, the semantics system 100 provides electronic control signals/commands to the TEM microscope to cause the TEM microscope to produce the particle image 160 in a desired manner (e.g., with a particular coordinate overlay, etc.).

The TEM microscope directs the beam at the sample and detects electrons scattered from the beam by the sample to produce the particle image 160. Thus, in one approach, the TEM generates the particle image 160 according to detections of electron scatter patterns (i.e., diffraction patterns) at different locations on the particle. That is, the semantics system 100 may control the TEM microscope to scan/sweep or otherwise move a focus of the beam across the particle. In one approach, the TEM microscope scans the particle to generate the image 160 using a two-dimensional (e.g., x-y coordinate plane) scan plane over the particle. The semantics system 100 may control placement of the scan plane over the particle. For example, in one aspect, the semantics system 100 adjusts a field of view of the TEM microscope by modifying the placement of the scan plane over the image. As one example, consider FIG. 2, which illustrates an example of the particle image 160. As shown, a particle 200 is depicted within an image having dimensions in an x-y coordinate plane.

Moreover, each separate point in the scan plane represents a detection by the TEM microscope that the semantics system 100 uses to construct the particle image 160. As noted, the TEM microscope produces a diffraction pattern (e.g., diffraction pattern 210) at each scan point of the particle representing how the particle scatters the electrons at that corresponding point. Thus, the particle image 160 is comprised of a plurality of diffraction patterns with each separate diffraction pattern being associated with a separate pixel in the image 160. For example, in an image having 1000 pixels by 1000 pixels, the image 160 would include 1,000,000 separate diffraction patterns assuming the image 160 is completely consumed by the particle. It should be appreciated that the particle image 160 may have more data dimensions than a 2D array of diffraction patterns in each pixel. For example, the particle image 160 may also include multiple color channels in addition to the diffraction patterns.

Figure 2:
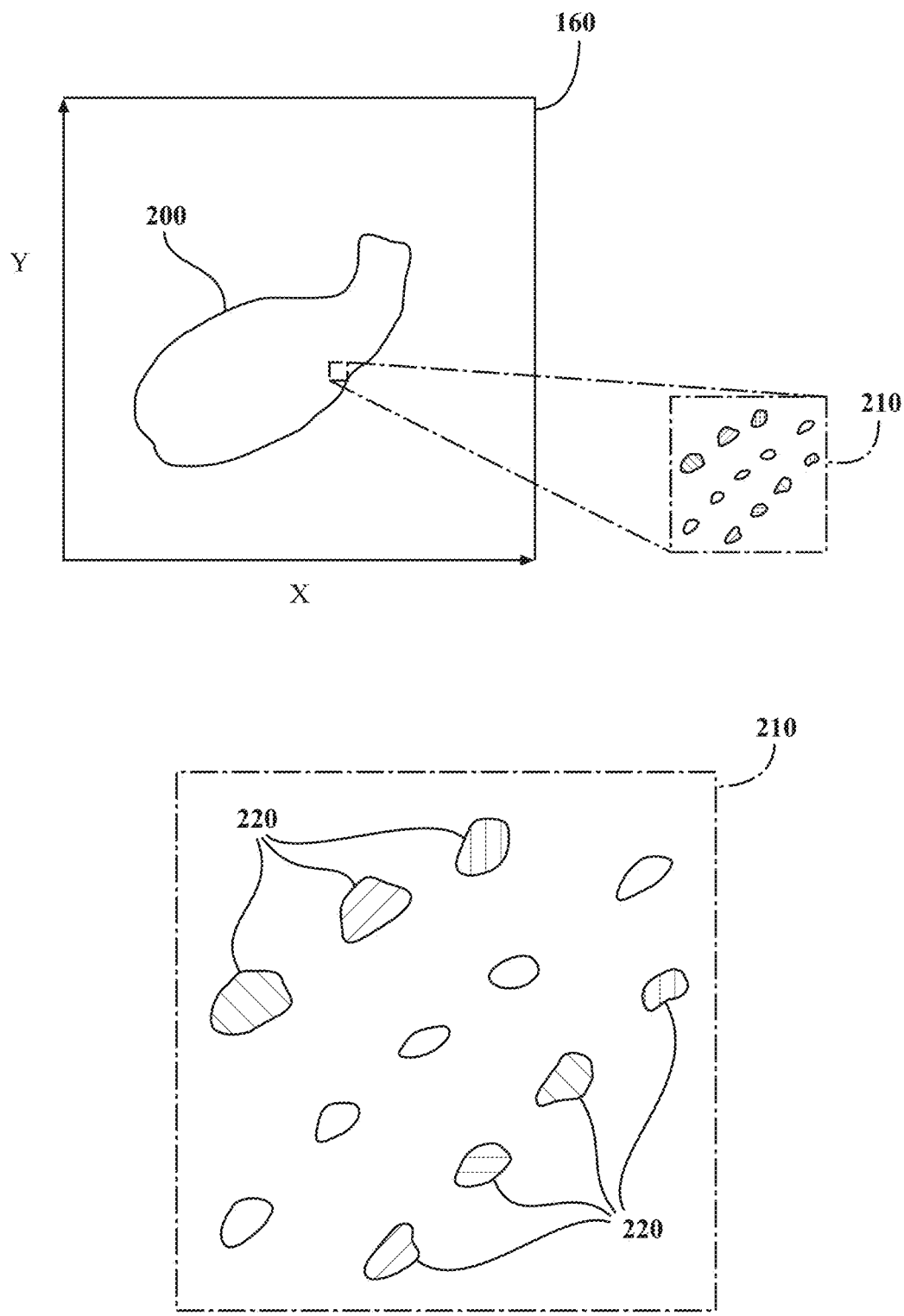
FIG. 2 illustrates one example of a particle image including diffraction patterns.

The diffraction patterns themselves are indicative of different traits of the particle at the associated locations. In one embodiment, the diffraction patterns are 512×512 pixels with separate pixels of the diffraction pattern indicating detection points of electrons on the detector. As one example, the diffraction pattern 210 of FIG. 2 represents a single detection point on the particle 200 and the separate points 220 illustrated within the diffraction pattern 210 are representative of electrons detected by the TEM microscope. Accordingly, the diffraction pattern represents positions, and spacings of detected electrons as scattered by a probed location on the particle. The various patterns depicted by the diffraction patterns are indicative of various properties of the particle at the particular location such as crystallographic structure, chemical properties, density, energy, and so on. Accordingly, the particle image 160 includes an aggregation of many diffraction patterns that embody characteristics of the particle.

With further reference to the semantics system 100, in one embodiment, the segmentation module 130 includes instructions that function to control the processor 110 to generate the segmented image 180 from the particle image 160 using at least the model 170. For example, the segmentation module 130 processes the particle image 160 using the model 170, which analyzes the particle image 160 according to internal understandings developed through training the model 170 on, for example, similar pre-labeled data.

Thus, prior to analyzing the particle image 160 to identify the characteristics, the semantics system 100 trains the model 170. Training the model 170 is generally undertaken as an initialization step but may also occur in an ongoing manner. The particular approach to training the model 170 undertaken by the system 100 can take different forms such as supervised, self-supervised, or unsupervised. The various approaches employ different mechanisms such as the noted training data that includes pre-applied labels in contrast to unsupervised forms that employ, for example, adversarial algorithms (e.g., discriminators) that challenge results produced by the model 170 according to a defined metric.

In either case, the semantics system 100 trains the model 170 to develop an internal understanding of the particle images 160 that the semantics system 100 leverages to improve identification of the characteristics of the associated particles. The model 170 embodies the internal understandings through developing various internal weights (e.g., hyper-parameters) of different nodes along with, for example, adjusting parameters of other functions and internal determinations. In one approach, the semantics system 100 determines errors between pre-labeled portions of an image and results provided by the model 170, which are then backpropagated into the model 170 in order to adjust internal values. In one approach, the model 170 is a convolutional neural network or other machine learning algorithm that recognizes aspects of an image to produce identifications therefrom. For example, the segmentation module 130 in concert with the model 170 perform semantic segmentation over the particle image 160 in order to identify characteristics of the particle associated with the individual pixels and group the pixels into subregions of like kinds.

Figure 3:
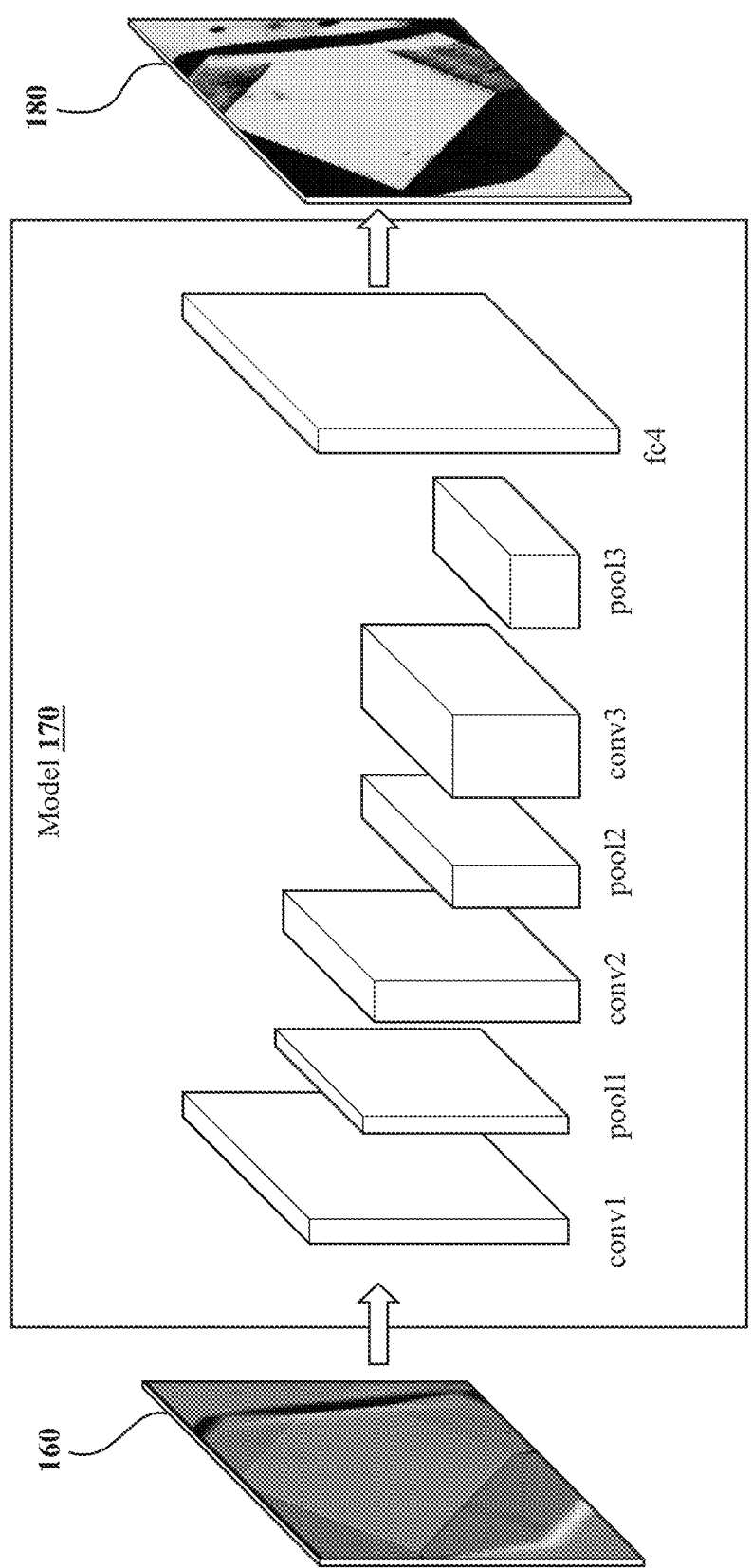
FIG. 3 illustrates an example of a network architecture of a model that can be employed to analyze particle images.

FIG. 3, illustrates one example of the model 170 as may be implemented by the semantics system 100. As illustrated in FIG. 2, the model 170 includes multiple different internal layers. The layers of the model 170 can include different combinations of convolutional layers, pooling layers, ReLU (rectified linear unit) layers, activation functions, skip connections between layers, pre-processing layers (e.g., size and/or color scale adjustments), post-processing layers (e.g., resolution adjustments), classification/fully connected layers, and so on. FIG. 2 illustrates an exemplary configuration that is in the spirit of the present approach but is not intended as a limiting example. For example, while not illustrated, the present approach may initially include a deconvolution that expands the individual pixels to represent the underlying diffraction patterns. Thus, as an initial processing step, the segmentation module 130, in one approach, implements the model 170 to initially expand the pixels by 512×512 to fully represent the underlying diffraction patterns.

Alternatively, the model 170 may include multiple deep learning networks with a first trained to identify/classify diffraction patterns according to associated characteristics whereas the second identifies/classifies groups of pixels according to the identified underlying diffraction patterns. In still further embodiments, the model 170 includes a third classifier to identify semantics from a segmented image 180 produced by other aspects of the model 170. Whichever approach is employed within the network architecture of the model 170, the segmentation module 130 implements the model 170 to accept the particle image 160 as an electronic input, process the image 160 according to the configuration of layers, and learned weightings/parameters, and produce a segmented image 180 as an electronic output thereof.

The segmented image 180 represents at least subregions/groups within the particle image where pixels/diffraction patterns have like characteristics either overall or in combination. That is, the segmentation module 130 uses the model 170 to identify which areas of the particle image 160 have similar characteristics. The result of this analysis by the module 130 is the segmented image 180 which is labeled according to the characteristics and subregions. As a general matter, the segmentation module 130 labels each pixel in the particle image 160 to identify characteristics of the locations associated with the pixels and also groups the pixels according to the characteristics where the characteristics represent particle-level attributes. Thus, in the simplest form, subregions are comprised of pixels having like characteristics, whereas in more complex forms, the model 170 identifies combinations of pixels that define subregions have particular characteristics. That is, in one embodiment, the subregions may having varying combinations of pixels depending on aspects identified by the model 170 as learned through the training process.

Figure 4:
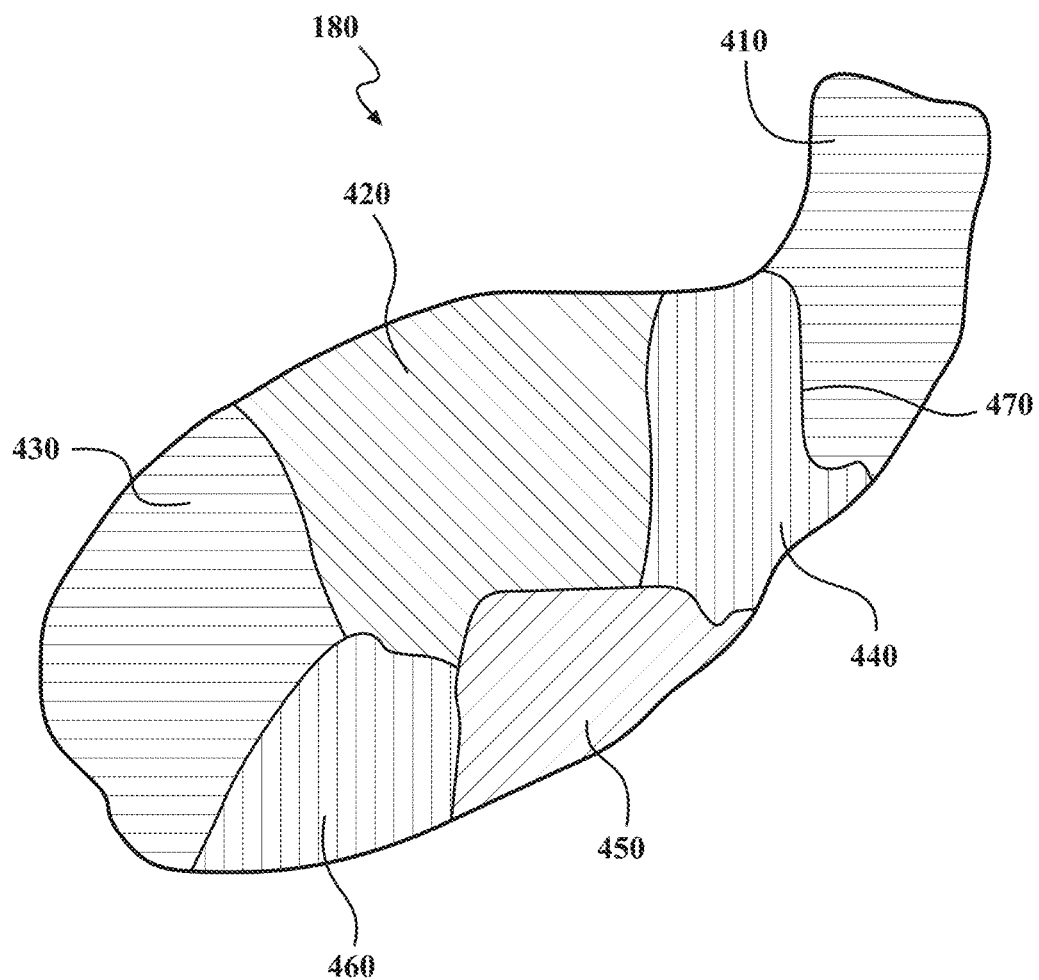
FIG. 4 illustrates one example of a segmented image.

One example of the segmented image 180 is illustrated in FIG. 4. As shown, the segmented image 180 of FIG. 4 includes a plurality of subregions 410, 420, 430, 440, 450, and 460 which are divided by boundaries such as boundary 470. Thus, the bounded subregions generally include pixels having similar characteristics and thus map to locations on the particle having similar characteristics. Thus, the segmented image 180 intrinsically indicates boundaries between abutting subregions having distinct characteristics. Although, the segmentation module 130, in one embodiment, further emphasizes/identifies the boundaries with particularity by integrating additional labels along such boundaries.

Moreover, the particular characteristics include, for example, crystallographic parameters, physical structure, chemical identity, electronic structure, material density, electron phase shift/spin, and other traits that are embodied within the particle image 160 or derived from relationships embodied within areas of various characteristics. The resulting segmented image 180 identifies the various characteristics of the underlying particle which can then be leveraged by further modules to infer further characteristics (e.g., semantics) of the particle.

Turning to the prediction module 140, in one embodiment, the prediction module 140 includes instructions that function to control the processor 110 to identify semantics of the particle according to at least boundaries between the subregions as depicted in the segmented image 180. In addition to identifying characteristics from the particle image 160, the semantics system 100 leverages relationships identified in the segmented image 180 to infer further aspects about the particle. That is, in one embodiment, the prediction module 140 analyzes the segmented image 180 to predict semantics (i.e., physics) of various aspects of the particle.

For example, the semantics define points of stress/strain in the particle from mismatched abutting subregions (i.e., subregions having different characteristics), electrically resistive regions, weakly bound regions (i.e., chemically bound), electrically charged regions, and similar semantics of the particle. In general, the semantics are aspects that are, for example, indicative of behaviors of the particle in relation to material physics and thus how the particle reacts to various environmental conditions over time, and/or interacts with other particles. Thus the semantics may be indicative of potential points of degradation/weakness, suitability for various purposes (e.g., as a battery component, as a resistive coating, etc.), and so on.

As such, the prediction module 140 analyzes the boundaries according to characteristics of the abutting subregions in order to determine corresponding semantics that correlate with such a boundary. In further aspects, the prediction module 140 further accounts for particular geometries of the boundaries, and/or geometries of the subregions in order to predict the semantics and/or the degree to which the particle exhibits a particular semantic. As one example, geometries of subregions and associated boundaries can influence an extent to which a particular type of semantic is present. That is, a brief/short boundary between to subregions may indicate a relatively weak semantic whereas an extended/large boundary may indicate a stronger semantic or at least probability of a semantic. Moreover, the prediction module 140, in one approach, executes the indicated prediction about the semantics using the model 170 or at least a portion thereof. For example, in one approach, the prediction module 140 is integrated with one or more classification layers that follow the segmentation layers of the model 170.

Of course, in a similar manner as discussed in relation to the identification of the characteristics, the semantics system 100 also, in one embodiment, trains the model 170 to identify the semantics associated with the boundaries. Accordingly, depending on a particular approach to training, the semantics system 100 trains the model 170 using pre-labeled training data that indicates semantics of a depicted particle along with, for example, boundaries and characteristics of associated subregions. Additionally, while the prediction module 140 is discussed as using the model 170, in further aspects, the prediction module 140 implements a second machine learning algorithm that predicts the semantics of the particle from the segmented image 180. Accordingly, the prediction module 140 employs a convolutional neural network or similar machine learning algorithm that analyzes images and classifies aspects of the images according to information provided therein.

As such, the semantics system 100 functions to identify the characteristics of the particle and the associated semantics when provided with just the particle image 160. In this way, the prediction module 140 further leverages the information about the particle embodied within the particle image 160 to streamline analysis of the particle and extrapolate semantics of the particle from learned correlations.

Figure 5:
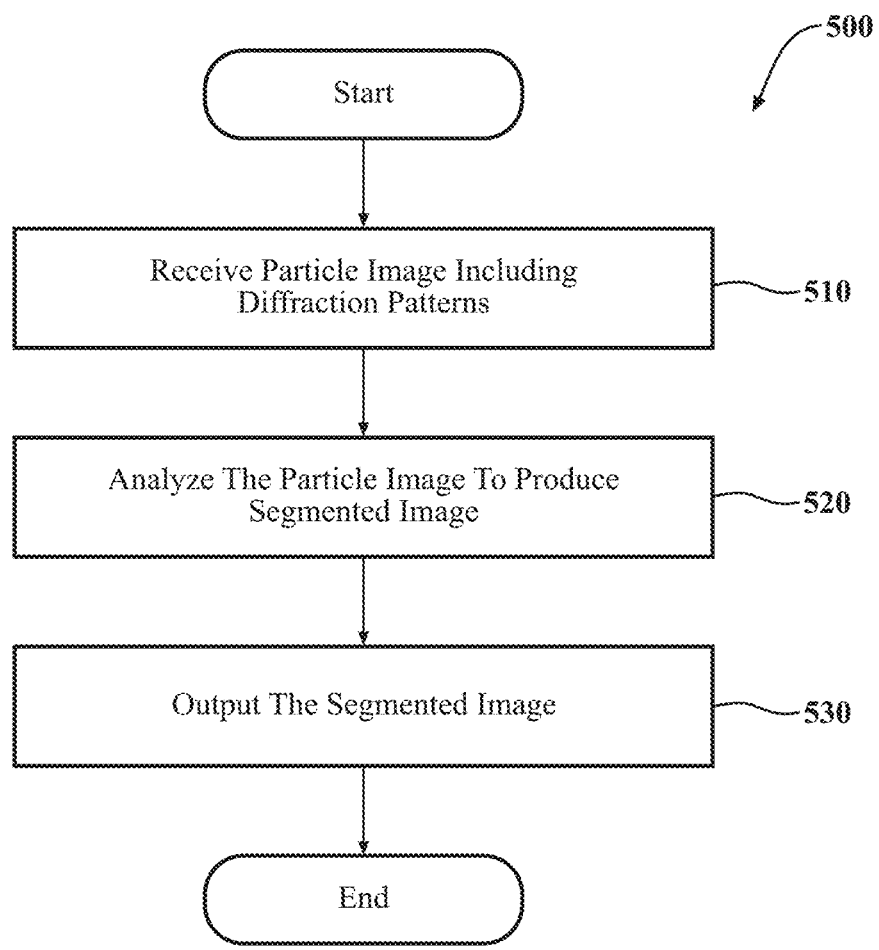
FIG. 5 illustrates one embodiment of a method associated with analyzing images to identify characteristics of an associated particle.
Figure 6:
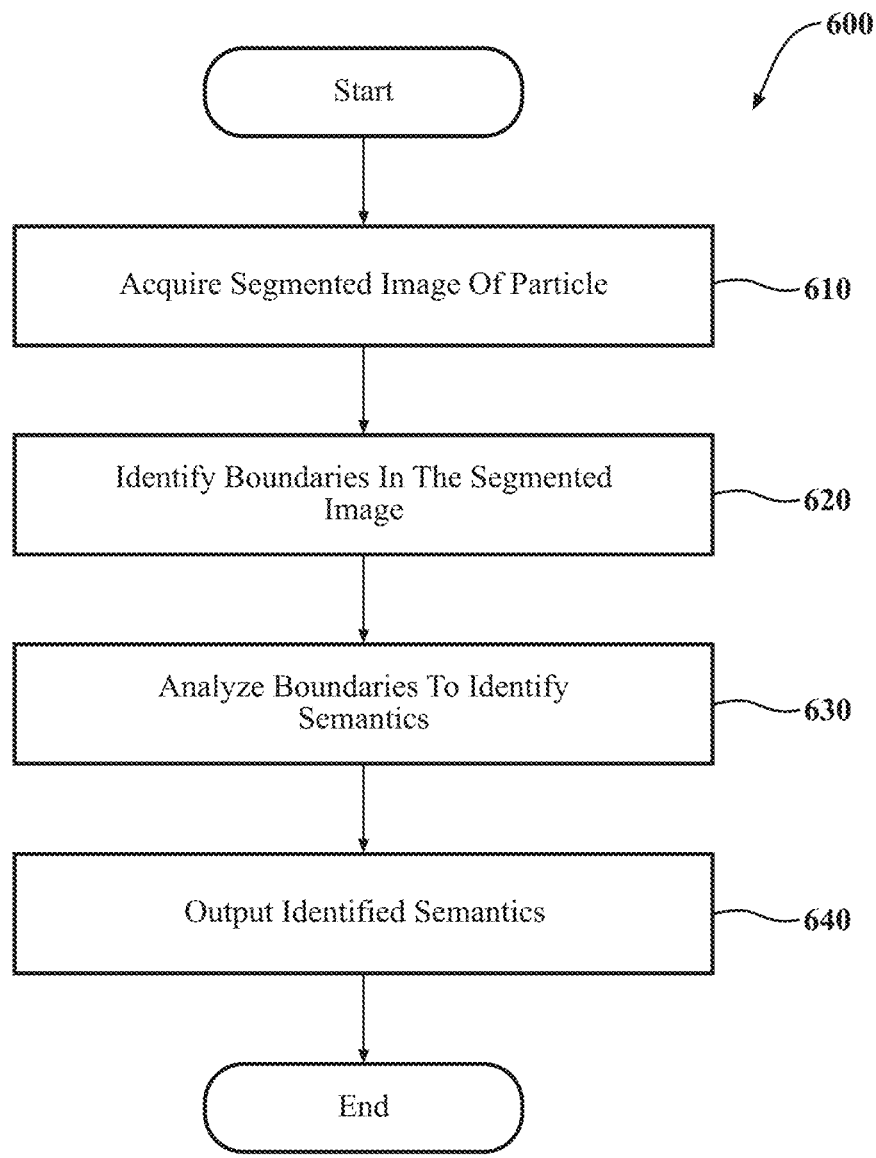
FIG. 6 illustrates one embodiment of a method associated with analyzing segmented images to identify semantics of an associated particle.

Additional aspects of inferring semantics of a particle from a particle image will be discussed in relation to FIGS. 5, and 6. FIG. 5 illustrates a flowchart of a method 500 that is associated with identifying characteristics of a particle as embodied within a particle image (e.g., TEM image 160). FIG. 6 illustrates a method 600 associated with inferring semantics (i.e., physics) of the particle from the segmented image embodying the characteristics of the underlying particle. Methods 500 and 600 will be discussed from the perspective of the semantics system 100 of FIG. 1. While methods 500 and 600 are discussed in combination with the semantics system 100, it should be understood that the methods 500/600 are not limited to being implemented within the semantics system 100 but is instead one example of a system that may implement the methods 500 and 600.

As a point about the initial configuration of the present approach, in one embodiment, the semantics system 100, prior to undertaking the methods 500 and 600, executes a training process to train one or more machine learning algorithms (e.g., model 170). As previously described, the semantics system 100 can be implemented to undertake different approaches to training the one or more machine learning algorithms such as unsupervised, supervised, or other suitable approaches. For example, in a supervised approach, the semantics system 100 uses a training dataset that is comprised of pre-labeled/segmented particle images. Thus, the semantics system 100 iteratively processes images from the training set according to the methods 500/600 and compares results with the provided labels to assess an error in the output. The semantics system 100 then, for example, backpropagates the errors to adjust internal understanding (i.e., nodal weights/hyper parameters and other parameters) of the machine learning algorithm according to a particular error function (e.g., gradient descent). In this way, the semantics system 100 trains the model 170 to recognize the desired aspects of the particle through analysis of the associated image.

At 510, the semantics system 100 receives the particle image 160. The semantics system 100 can receive the particle image 160 through either active acquisition (i.e., controlling a device to acquire the particle image 160 of the particle) or through communication of the particle image 160 via a data communication link. Thus, in one approach, the semantics system 100 actively controls a transmission electron microscope to scan a sample and produce the particle image 160 therefrom. In further aspects, the particle image 160 is electronically stored as a collection of images of the particle or other particles acquired under, for example, various conditions. Thus, the acquisition of the particle image 160 can be either an active task or separate process.

In either case, as previously mentioned, the particle image 160 is comprised of a multiplicity of pixels (e.g., 1024×1024, 2048×2048, or another suitable resolution) that can each include a separate diffraction pattern and/or other modalities (e.g., color, depth, etc.). Thus, the particle image 160 represents a dense/fine-grained portrayal of information about an associated particle especially considering that the diffraction patterns can separately have resolutions of 512×512 pixels/detection points. Of course, while the diffraction patterns are discussed as separate patterns/images that comprise pixels of the image 160, in one embodiment, the diffraction patterns are provided with differing resolutions depending on a particular detector employed to detect scattered electrons.

At 520, the segmentation module 130 analyzes the particle image 160. In one embodiment, the segmentation module 130 analyzes the particle image 160 by convolving one or more filters over the image 160 to identify features embodied therein. The process of convolving filters and recognizing characteristics of the particle is, for example, embodied within the model 170 and may be supported by functionality of the segmentation module 130. That is, the segmentation module 130 uses the model 170, which includes a machine learning algorithm such as a CNN, to analyze the particle image 160. The analysis of the image 160 can involve a multiplicity of separate processes from pre-processing steps, to filtering/convolving, pooling, classification, up-sampling, and so on.

In one approach, the segmentation module 130 performs pre-processing on the image 160 to improve the form in which the image 160 is provided into the model 170. Thus, the segmentation module 130 may adjust colors, correct distortions or perform other pre-processing functions such as deconvolving the image 160 to fully represent the diffraction patterns in place of the separate pixels. Moreover, in one approach, instead of deconvolving the image 160, the segmentation module 130 performs an initial classification pass over the image 160 by processing each separate diffraction pattern. For example, the segmentation module 130 processes the diffraction patterns independently to classify one or more characteristics of the particle identified therein. That is, instead of initially processing the image 160 as a single unit, the segmentation module 130 along with an architecture of the model 170 are configured to separately process the diffraction patterns and use the generated classification to define each pixel of the image 160 according to identified aspects of the corresponding diffraction patterns.

A resulting intermediate image, in one embodiment, includes representations of the diffraction patterns at corresponding pixel locations. The intermediate image includes, for example, determinations about the diffraction patterns identifying associated characteristics of the particle that replace the diffraction patterns in the image 160. Thus, in one approach, the segmentation module 130 initially processes the diffraction patterns to produce the intermediate image using annotations identifying the characteristics. The annotations within the intermediate image effectively simplify the particle image 160 into a refined representation with characteristics of correlating locations on the particle being represented within corresponding pixels in place of the diffraction patterns.

Thus, the segmentation module 130 can then proceed with performing semantic segmentation over the intermediate image (i.e., partially processed particle image 160) to identify the subregions of characteristics within the particle. Otherwise, the segmentation module 130 produces the intermediate image from the pre-processed image 160 that, for example, includes the diffraction patterns in a deconvolved/integrated form or another suitable form for processing by the segmentation module 130 and the model 170.

In either case, the segmentation module 130 uses the model 170 to analyze the partially processed particle image 160 in order to group similarly situated pixels into subregions. The segmentation module 130 defines the subregions according to groups of pixels in the particle image 160 having similar characteristics. Thus, the segmentation module 130 generally forms the subregions as learned from training on other particle images with labeled pixels and subregions. Of course, in further approaches, the segmentation module 130 may define the subregions according to a "best-fit" for separate groups of pixels.

As such, in various implementations, the segmentation module 130 can accept varying levels of conformity/heterogeneity in the different subregions. In other words, the segmentation module 130 may group the pixels according to one or more approaches that result in the subregions generally defining areas in the particle that have similar characteristics but may include one or more pixels with differing characteristics as may be necessary to form the subregions. Of course, the particular approach may be customized such that subregions are wholly exclusive and group only like kind characteristics or are selectively inclusive to a defined extent. In still further aspects, as noted, the subregions are defined according to learned representations of how the subregions generally occur across a population of particles as exhibited in the training data.

As an additional aspect, the segmentation module 130, in one embodiment, undertakes further refinement of the subregions by rescanning areas proximate to boundaries between subregions with the microscope. That is, if a particular pixel overlaps a boundary between regions, the segmentation module 130 can adjust coordinates of nearby pixels (e.g., slide the coordinate plane) such that the overlap is minimized and thus the pixel is wholly within a particular subregion. By adjusting the positioning of a pixel to conform with a boundary between subregions, an associated diffraction pattern that the semantics system 100 acquires through re-imaging the particle better represents characteristics of the pixel abutting the boundary instead of including overlapping characteristics of two different subregions. Thus, while the segmentation module 130 may not increase a resolution to further resolve characteristics of a pixel, the segmentation module 130, in one embodiment, does further resolve the pixel through adjustment of overlaps between different pixels that neighbor a boundary.

At 530, the segmentation module 130 provides the segmented image 180 as an electronic output. In one embodiment, the segmented image 180 is provided to the prediction module 140. Alternatively, or additionally, in one approach, the segmented image 180 is stored in the database 150 or another suitable electronic data store. In either case, the segmentation module 130 provides the segmented image 180 with associated labels that provide, for example, a pixel-by-pixel indication correlating with the particle image 160 of characteristics associated with the pixel (e.g., physical trait and corresponding subregion).

Accordingly, the semantics system 100 loads or otherwise receives the training set that is comprised of the custom images as previously described. In one embodiment, the semantics system 100 generates the training set and stores the training set until needed. Thus, the semantics system 100 loads the training set which is comprised of a plurality of custom images. As previously mentioned, the custom images may be initially generated to be directed at depictions of subject matter that relates to a particular task of a module being trained. Thus, the custom images can depict particular selected subject matter that relates to training the module on a specific task (e.g., obstacle detection, collision avoidance, etc.).

Turning now to the method 600, as described above, as an initialization process, the semantics system 100, in one embodiment, trains the model 170 or another machine learning algorithm to identify semantics of the particle by analyzing the segmented image 180. In particular, the semantics system 100 trains a machine learning algorithm or at least portion thereof to identify semantics of the particle according to attributes of boundaries between subregions. Thus, in one approach, the semantics system 100 uses segmented images with labels identifying semantics in relation to individual and/or combinations of boundaries. Moreover, the individual boundaries defining semantics according to characteristics of abutting subregions. Thus, the semantics system 100, in one approach, trains the model 170 or another machine learning algorithm to classify the semantics according to attributes of the boundaries.

At 610, the prediction module 140 acquires the segmented image 180. As previously described, the segmented image 180 is segmented into subregions grouping locations on the particle of similar characteristics. In general, the prediction module 140 can accept the segmented image 180 directly from the segmentation module 130 or from a data store that includes a set of images that were previously segmented. In either case, the input to the prediction module 140 is an image including pixels labeled according to characteristics correlating with associated locations on the particle.

At 620, the prediction module 140 identifies boundaries in the segmented image 180 between subregions. In one embodiment, the prediction module 140 maps the boundaries by identifying where distinct subregions interface. The prediction module 140 can then, in one approach, annotate the separate boundaries according to particular characteristics such as types of the abutting subregions (i.e., labeled characteristics), particular geometries, and/or other notable attributes. Of course, in further aspects, the prediction module 140 performs the noted analysis at 620 according to internal functions of the model 170 and learned/trained understandings embodied therein for identifying various aspects of the segmented image 180.

At 630, the prediction module 140 identifies semantics of the particle. In one embodiment, the prediction module 140 analyzes at least the boundaries between the subregions to infer the semantics of the particle. As previously mentioned, the semantics define expected behaviors of the particle in relation to material physics such as electrical properties, mechanical stresses, electrochemical properties, and so on. Thus, the boundaries between regions of the particle define interfaces between areas having different characteristics that generally inform how the particle behaves i.e., the semantics/physics of how the particle exists. Consequently, the prediction module 140 in combination with the model 170 or another purpose-built machine learning algorithm process the segmented image 180, and, in particular, information about the boundaries to predict the semantics of the particle. Thus, the prediction module 140 considers the attributes of the boundaries to derive the semantics through the learned understanding of the model 170.

It should be appreciated that while the semantics are generally referred to in relation to the particle as a whole, in one embodiment, the prediction module 140 indicates the semantics with particularity in relation to specific boundaries and/or subregions associated with the boundaries. Additionally, it should be noted that the model 170 can include additional classification layers that add additional functionality over the basic segmentation functionality discussed in relation to FIG. 5 for the purpose of inferring the semantics. Moreover, as indicated, the prediction module 140, in one approach, instead implements a separate semantics classification model in addition to the model 170. In either case, the prediction module 140 uses an implemented machine learning algorithm to analyze the segmented image 180, at 630, according to characteristics of abutting regions, particular aspects of the boundary itself, and so on in order to determine the semantics.

At 640, the prediction module 140 generates an electronic output identifying the semantics. In one embodiment, the prediction module 140 generates the electronic output by integrating the semantics as labels within the segmented image 180. That is, the prediction module 140 modifies the segmented image 180 to integrally combine identifiers of the semantics into the image 180. In this way, the semantics system 100 provides a streamlined mechanism for ascertaining various aspects of a particle from a simple image of the particle.

In further embodiments, the semantics system 100 implements a further analysis of the segmented images to predict effects of a stimulus on a particle. That is, the semantics system 100 implements an additional machine learning algorithm in the form of a generative network. The generative network (i.e., GAN) accepts inputs in the form of a particle image and, for example, an identified stress. The network can then produce a predicted physical form and associated characteristics of the particle as though the particle had been subjected to the stress. For example, in one approach, a method includes, in response to receiving a particle image, analyzing the particle image to identify semantics of the particle including producing a segmented image that indicates characteristics of subregions within the particle. The method further includes predicting changes in the characteristics from the stimulus being applied to the particle by applying a stimulus model to the segmented image. Predicting the changes includes generating a predicted image of the particle according to the changes in the characteristics. Additionally, the method includes providing the predicted image as an electronic output.

In further aspects, the stimulus is a stress applied to the particle that effects a physical structure of the particle including the semantics and the characteristics. Generating the predicted image includes generating the predicted image with segments identifying the subregions as modified according to the stimulus. The stimulus model is a machine learning algorithm that accepts the segmented image as an electronic input and generates the predicted image to simulate effects of the stimulus on the particle. Predicting the changes includes predicting how the semantics are altered through inferences embodied in the stimulus model about how at least the characteristics of the particle respond to the stimulus. The stimulus includes one of heat, mechanical stress, chemical exposure, and electrochemical effects, and wherein the stimulus model is trained to predict the changes for a single stress.

Receiving the particle image includes receiving the particle image from a transmission electron microscope (TEM) that scans the particle to produce the particle image. The particle image includes diffraction patterns that are patterns of electrons as scattered onto a detector in the TEM resulting from the electrons interacting with the particle at a location corresponding with a respective one of the pixels. In one approach, analyzing the particle image includes using a machine learning algorithm to perform semantic segmentation over the particle image and produce the segmented image. Identifying the semantics of the particle includes identifying relationships between the subregions that define the semantics for the particle. Identifying the semantics includes mapping properties of the boundaries between the subregions according to the characteristics of the particle within abutting ones of the subregions. The pixels of the particle image separately include diffraction patterns indicative of the characteristics of the particle including a physical structure of the particle at a corresponding location. To train the GAN, the semantics system, in one approach, uses two sets of images. The first set of images includes images prior to exposure to a training, using a pair of images for a plurality of particles depicting the particles in pre-stimulus and post-stimulus, the stimulus model to predict the changes, wherein the stimulus model is a generative adversarial network (GAN).

FIG. 1 will now be discussed in further detail as an example environment within which the system and methods disclosed herein may operate. The semantics system 100 can include one or more processors. In one or more arrangements, the processor(s) can be a main processor of the semantics system 100. For instance, the processor(s) can be an electronic control unit (ECU). The semantics system 100 can include one or more data stores for storing one or more types of data. The data store can include volatile and/or non-volatile memory. Examples of suitable data stores include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store can be a component of the processor(s), or the data store can be operably connected to the processor(s) for use thereby. The term "operably connected," as used throughout this description, can include direct or indirect connections, including connections without direct physical contact, electrical connections, optical connections, and so on.

The one or more data stores can include sensor data or other electronic data that is processed by a processor of the semantics system 100 at the direction of one or more modules implementing disclosed methods of the present disclosure. In this context, "electronic data" broadly refers to information produced by the semantics system 100 and that is received, for example, from various electronic sensors, electronic communications, electronic interactions with control systems and/or devices, and so on.

The semantics system 100 can include one or more modules. The modules can be implemented as computer-readable program code that, when executed by a processor, implement one or more of the various processes/methods described herein. One or more of the modules can be a component of the processor(s), or one or more of the modules can be executed on and/or distributed among other processing systems to which the processor(s) is operably connected. Moreover, in further examples, in one or more of the modules are embodied as ASICS, FPGAs, task-specific microprocessors, control units (e.g., ECU), and so on. The modules can include instructions (e.g., program logic) executable by one or more processor(s) and/or the module itself. Alternatively, or in addition, one or more data stores may include instructions that embody the modules.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-6, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across multiple interconnected processing systems. As a general matter, an electronic processing system or another apparatus adapted for carrying out the methods described herein may implement the disclosed approach(es). One combination of hardware and software may include a processing system with computer-usable program code that, when being loaded and executed, controls the processing system such that the processing system carries out the methods described herein. The systems, components and/or processes also can be embedded in a computer-readable storage mediums, such as a computer program product or other electronic storage device(s) that are capable of accommodating such computer program code. Furthermore, the computer-readable storage mediums are readable by a machine, tangibly embodying a program of instructions executable by the machine to perform methods and processes described herein.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A semantics system for classifying semantics of a particle, comprising:
   one or more processors;
   a memory communicably coupled to the one or more processors and storing:
   a segmentation module including instructions that when executed by the one or more processors cause the one or more processors to analyze a particle image to identify characteristics of the particle represented in respective pixels of the particle image and to produce a segmented image that groups the pixels into subregions; and
   a prediction module including instructions that when executed by the one or more processors cause the one or more processors to identify semantics of the particle according to at least boundaries between the subregions, wherein the semantics define expected behaviors of the particle in relation to material physics, and
   wherein the prediction module includes instructions to provide the segmented image including the semantics as an electronic output.

2. The semantics system of claim 1, wherein the segmentation module includes instructions to analyze the particle image including instructions to use a machine learning algorithm that is a convolutional neural network (CNN) to perform semantic segmentation over the particle image, and
   wherein respective ones of the subregions are formed from associated ones of the pixels corresponding to locations on the particle where the characteristics are at least similar, and
   wherein the characteristics include at least crystallographic parameters, chemical identity, electronic structure, material density, and electrochemical properties.

3. The semantics system of claim 1, wherein the pixels of the particle image separately include diffraction patterns indicative of the characteristics of the particle including a physical structure of the particle at a corresponding location, and
   wherein the particle image includes diffraction patterns that are patterns of electrons as scattered onto a detector in a transmission electron microscope (TEM) resulting from the electrons interacting with the particle at a location corresponding with a respective one of the pixels.

4. The semantics system of claim 3, wherein the segmentation module includes instructions to analyze the particle image including instructions to use a machine learning algorithm that convolves a filter over the diffraction patterns to identify which of the diffraction patterns correlate with ones of the characteristics, and
   wherein the prediction module includes instructions to identify the semantics of the particle including instructions to identify relationships between the subregions that define the semantics for the particle.

5. The semantics system of claim 1, wherein the prediction module includes instructions to identify the semantics including instructions to map properties of the boundaries between the subregions according to the characteristics of the particle within abutting ones of the subregions.

6. The semantics system of claim 1, wherein the prediction module includes instructions to identify the semantics including instructions to map the boundaries including instructions to dynamically control a transmission electron microscope to refine the particle image along the boundaries by re-imaging at least respective ones of the pixels that span the boundaries according to an adjusted scan grid that avoids pixels overlapping the boundaries.

7. The semantics system of claim 1, wherein the segmentation module includes instructions to train, using a set of training images depicting different particles and labeled according to associated segments and training semantics, a machine learning algorithm to segment the training images into the subregions and to identify the semantics according to boundaries between the subregions.

8. The semantics system of claim 1, wherein the segmentation module includes instructions to receive the particle image including instructions to receive the particle image from a transmission electron microscope (TEM) that scans the particle to produce the particle image.

9. A non-transitory computer-readable medium for classifying semantics of a particle and including instructions that when executed by one or more processors cause the one or more processors to:
   analyze a particle image to identify characteristics of the particle represented in respective pixels of the particle image and to produce a segmented image that groups the pixels into subregions;
   identify semantics of the particle according to at least boundaries between the subregions, wherein the semantics define expected behaviors of the particle in relation to material physics; and
   provide the segmented image including the semantics as an electronic output.

10. The non-transitory computer-readable medium of claim 9, wherein the instructions to analyze the particle image include instructions to use a machine learning algorithm that is a convolutional neural network (CNN) to perform semantic segmentation over the particle image, and
    wherein respective ones of the subregions are formed from associated ones of the pixels corresponding to locations on the particle where the characteristics are at least similar, and
    wherein the characteristics include at least crystallographic parameters, chemical identity, electronic structure, material density, and electrochemical properties.

11. The non-transitory computer-readable medium of claim 9, wherein the pixels of the particle image separately include diffraction patterns indicative of the characteristics of the particle including a physical structure of the particle at a corresponding location, and wherein the particle image includes diffraction patterns that are patterns of electrons as scattered onto a detector in a transmission electron microscope (TEM) resulting from the electrons interacting with the particle at a location corresponding with a respective one of the pixels.

12. The non-transitory computer-readable medium of claim 11, wherein the instructions to analyze the particle image including instructions to use a machine learning algorithm that convolves a filter over the diffraction patterns to identify which of the diffraction patterns correlate with ones of the characteristics, and wherein the instructions to identify the semantics of the particle include instructions to identify relationships between the subregions that define the semantics for the particle.

13. The non-transitory computer-readable medium of claim 9, wherein the instructions to identify the semantics include instructions to map properties of the boundaries between the subregions according to the characteristics of the particle within abutting ones of the subregions.

14. A method for classifying semantics of a particle, comprising:

in response to receiving a particle image, analyzing the particle image to identify characteristics of the particle represented in respective pixels of the particle image to produce a segmented image that groups the pixels into subregions;

identifying semantics of the particle according to at least boundaries between the subregions, wherein the semantics define expected behaviors of the particle in relation to material physics; and providing the segmented image including the semantics as an electronic output.

15. The method of claim 14, wherein analyzing the particle image includes using a machine learning algorithm that is a convolutional neural network (CNN) to perform semantic segmentation over the particle image, and wherein respective ones of the subregions include associated ones of the pixels corresponding to locations on the particle where the characteristics are at least similar, the characteristics including at least crystallographic parameters, chemical identity, electronic structure, material density, and electron phase shift.

16. The method of claim 14, wherein receiving the particle image includes receiving the particle image from a transmission electron microscope (TEM) that scans the particle to produce the particle image, wherein the pixels of the particle image separately include diffraction patterns indicative of the characteristics of the particle including a physical structure of the particle at a corresponding location, and wherein the particle image includes diffraction patterns that are patterns of electrons as scattered onto a detector in the TEM resulting from the electrons interacting with the particle at a location corresponding with a respective one of the pixels.

17. The method of claim 16, wherein analyzing the particle image includes using a machine learning algorithm and convolving a filter over the diffraction patterns to identify which of the pixels correlate with similar ones of the characteristics, and wherein identifying the semantics of the particle includes identifying relationships between the subregions that define the semantics for the particle.

18. The method of claim 14, wherein identifying the semantics includes mapping properties of the boundaries between the subregions according to the characteristics of the particle within abutting ones of the subregions.

19. The method of claim 14, wherein identifying the semantics includes mapping the boundaries by dynamically controlling a transmission electron microscope to refine the particle image along the boundaries by re-imaging at least respective ones of the pixels that span the boundaries according to an adjusted scan grid that avoids pixels overlapping the boundaries.

20. The method of claim 14, further comprising:

training, using a set of training images depicting different particles and labeled according to associated segments and training semantics, a machine learning algorithm to segment the training images into the subregions and to identify the semantics according to boundaries between the subregions.

* * * * *